United States Patent [19]

Elokdah et al.

[11] Patent Number: 5,654,436

[45] Date of Patent: Aug. 5, 1997

[54] 2-SUBSTITUTED BENZIMIDAZOLE DERIVATIVES

[75] Inventors: Hassan M. Elokdah, Fairless Hills, Pa.; Sie-Yearl Chai, Lawrenceville, N.J.; Theodore S. Sulkowski, Wayne, Pa.

[73] Assignee: American Home Products Corporation, Madison, N.J.

[21] Appl. No.: 477,842

[22] Filed: Jun. 7, 1995

[51] Int. Cl.$^6$ ............... C07D 401/04; C07D 235/12
[52] U.S. Cl. .................. 546/273.4; 548/310.1
[58] Field of Search ............... 514/395, 394, 514/477, 478; 548/301.7, 302.1, 314.7, 310.1; 546/273.4

[56] References Cited

U.S. PATENT DOCUMENTS

| | | |
|---|---|---|
| 4,814,329 | 3/1989 | Harsanyi et al. . |
| 5,128,359 | 7/1992 | Bru-Magniez et al. . |
| 5,171,748 | 12/1992 | Roberts et al. ............... 548/101 |
| 5,387,600 | 2/1995 | Aikawa et al. . |

FOREIGN PATENT DOCUMENTS

| | | |
|---|---|---|
| 1530439 | 6/1968 | France . |
| 4212748 | 10/1993 | Germany . |

OTHER PUBLICATIONS

Thomas et al. "New Nonpeptide Angiotensis II Receptor Antagonists . . . " J. Med. Chem. 1992, 35, 877–885.

Murray et al. "Inhibition of Rat Hepatic Microsomal Aminopyridine N–Demthylase Activity by Benzimidazol Derivatives Quantitative Structure Activity Relationships", Journal of Medicinal Chemistry, 25, 887–892 (1982).

*Primary Examiner*—Jeffrey Mullis
*Attorney, Agent, or Firm*—Arnold S. Milowsky

[57] ABSTRACT

Disclosed herein are compounds of the formula:

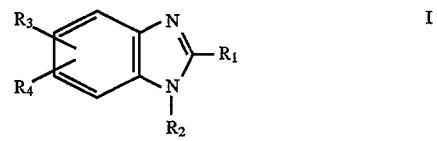

where $R_1$ is alkyl, trifluoromethyl or pyridinyl;

$R_2$ is H, alkyl or substituted arylalkyl, in which the substituents are one or two halogens, carboxyl or alkoxycarbonyl groups;

$R_3$ and $R_4$ are H, alkyl, halogen or nitro;

or a pharmaceutically acceptable salt thereof, which are useful as inhibitors of smooth muscle cell proliferation.

6 Claims, No Drawings

2-SUBSTITUTED BENZIMIDAZOLE DERIVATIVES

BACKGROUND OF INVENTION

Proliferation and directed migration of vascular smooth muscle cells are important vascular occlusive components in such processes as hypertension-induced vascular remodeling, vascular restenosis, and atherosclerosis (Gibbons, G. H.; Dzau, V. J.; NEJM, 1994; 330: 1431). The overall disease process is referred to as hyperproliferative vascular disease based on the etiology of the disease process. Vascular occlusion is preceded by stenosis resulting from intimal smooth muscle cell hyperplasia (Clowes, A. W.; Reidy, M. A.; J. Vasc. Surg., 1991, 13: 885). The underlying cause of intimal smooth muscle cell hyperplasia is vascular smooth muscle cell injury leading to disruption of the endothelium and extracellular matrix (Schwartz, S. M., Human Pathology, 1987; 18: 240; Fingerle, J., Arteriosclerosis, 1990; 10: 1082). Normally, the cells of the arterial wall are under close negative control and in a low basal proliferating state or in a quiescent non-proliferating state. Following vascular injury, the release of growth factors and cytokines result in smooth muscle cell proliferation and migration (Fagin, J. A.; Forrester, J. S., Trends in Cardiovascular Med., 1992; 2; 90.; Shiratani, M.; Yui, Y.; Kawai, C., Endothelium, 1993; 1: 5).

Vascular injury leading to intimal hyperplasia can be induced immunologically or by invasive cardiovascular procedures. Atherosclerosis is a common form of biologically mediated vascular injury progressing to stenosis. Abnormal proliferation of vascular smooth muscle cells is a feature of atherosclerotic plaques responsible for obstructive neo-intimal lesions at the site of intimal damage (Ross, R., Nature, 1993: 362; 801; Cascells, W., Circulation, 1992; 86: 723). Mechanical injury leading to intimal hyperplasia can occur following angioplasty procedures, organ transplant surgery and other vascular invasive procedures that disrupt vascular integrity (Clowes, A. W.; Reidy, M. A., J. Vasc. Surg., 1991; 13: 885; Isik, F. F.; McDonald, T. O.; Ferguson, M.; Yanaka, E., Am. J. Pathol., 1992; 141: 1139).

Percutaneous transluminal coronary angioplasty has achieved wide acceptance for the treatment of coronary artery stenosis. In this procedure the endothelium is damaged and exposed to a variety of chemoattractants and mitogens which are either blood-borne or are released at the site of injury. Among these agents, platelet-derived growth factor (PDGF) is thought to play a significant role in the process of smooth muscle cell proliferation and chemotaxis (Reidy, M. A.; Fingerle, J.; Lindner, V.; Circulation, 1993:86 (suppl III): III-43.; Ferns, G. A. A.; Raines, E. W.; Sprugel, K. H.; Montani, A. S.; Reidy, M. A.; Ross, R.; Science, 1991; 253: 1129.; Jawien, A., et al., J. Clin. Invest., 1992; 89: 507; Nabel, E. G., et al., J. Clin. Invest., 1993; 91: 1822). Within 3 to 6 months after angioplasty, a significant reduction in blood flow occurs in approximately 30–40% of patients as a result of restenosis caused by response to vascular injury during this procedure. These patients then require a second interventional procedure (Pepine, C., Circulation, 1990; 81: 1753.; Hardoff, R. J., J. Am. Coll. Cardiol., 1990; 15: 1486). Accordingly, agents that limit the restenosis process would be of significant benefit. Agents that inhibit vascular smooth muscle cell proliferation, particularly PDGF-stimulated proliferation, would be useful in the treatment of vascular hyperproliferative disorders (Molloy, C. J., Drug Dev. Res., 1993; 29: 148.; Newby, A. C.; George, S. J., Cardiovasc. Res., 1993; 27:1173).

U.S. Pat. No. 5,387,600, discloses 2-alkyl or heterocyclyl-benzimidazoles of formula I as ACAT inhibitors:

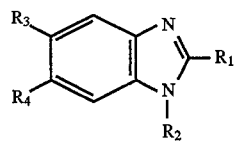

U.S. Pat. No. 5,128,359 discloses 1-benzylbenzimidazol-2-alkanoic acid derivatives for treatment of atherosclerosis.

U.S. Pat. No. 4,814,329 discloses 2-thiobenzimidazoles of following formula II as anti-hyperlipidemic agents, where R is $C_1$–$C_4$ alkyl and $C_2$–$C_4$ hydroxyalkyl:

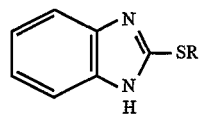

DE 4212748, discloses N-biphenymethyl benzimidazoles as AII antagonists.

DESCRIPTION OF THE INVENTION

In accordance with this invention there is provided a group of 2-substituted benzimidazole derivatives that are useful as smooth muscle cell proliferation inhibitors and as therapeutic compositions for treating diseases and conditions which are characterized by excessive smooth muscle cell proliferation, such as restenosis. The 2-substituted benzimidazoles of this invention present the structure of formula I:

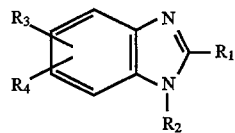

where $R_1$ is alkyl of 1 to 6 carbon atoms, trifluoromethyl or pyridinyl; $R_2$ is H, alkyl of 1 to 6 carbon atoms or substituted arylalkyl of 7 to 10 carbon atoms, in which the substituents are one or two halogens, carboxyl or alkoxycarbonyl groups of 2 to 7 carbon atoms; $R_3$ and $R_4$ are H, alkyl of 1 to 6 carbon atoms, halogen or nitro; or a pharmaceutically acceptable salt thereof. The preferred substituted arylalkyl moiety is a substituted benzyl group.

The 1,2-disubstituted benzimidazoles of this invention are prepared according to the general sequence of reactions outlined in the scheme below:

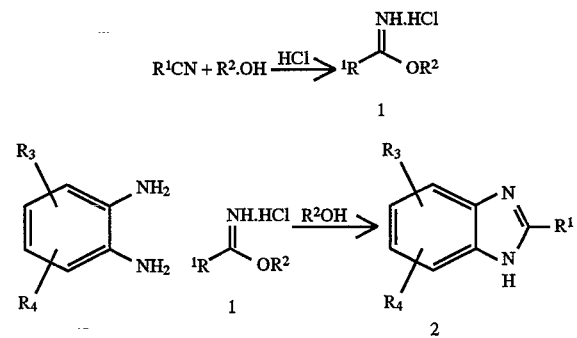

-continued

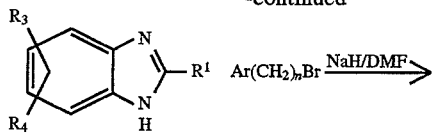

2

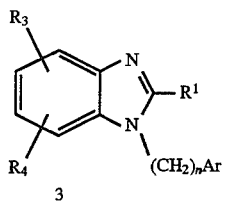

3

The imino ether hydrochloride (1) is prepared by reacting an appropriate nitrile with an alcohol and hydrogen chloride at 0° C. Reaction of 1 and an appropriately substituted 1,2-diaminobenzene in refluxing ethanol affords the corresponding 2-substituted benzimidazole (2). Alkylation of 2 with an appropriately substituted arylalkyl halide, where n is 1, 2 or 3, in dimethyl formamide using sodium hydride as base affords the 1,2-disubstituted benzimidazoles (3) of this invention.

The pharmaceutically acceptable acid addition salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids. With those compounds possessing an acidic substituent such as the carboxylic acids, the pharmaceutically acceptable salts include the alkali metal salts (sodium or potassium), the alkaline earth metal salts (calcium or magnesium) and ammonium salts.

This invention includes pharmaceutical compositions comprised of the benzimidazoles of the invention either alone or in combination with excipients (i.e. pharmaceutically acceptable materials with no pharmacological effect). Such compositions are useful in treating diseases which are characterized by excessive smooth muscle cell proliferation most frequently arising from vascular reconstructive surgery and transplantation, for example, balloon angioplasty, vascular graft surgery, coronary artery bypass surgery, and heart transplantation. Other disease states in which there is unwanted vascular proliferation include hypertension, asthma, and congestive heart failure. The compounds of this invention are thus useful for treating these diseases and states.

The compounds of this invention may be administered systemically, for example by intravenous injection, typically ranging from 0.1 to 10 mg/kg/h over 5–30 days, by subcutaneous injection at lower dose or by oral administration at higher dose than intravenous injection. Localized delivery of the compounds of this invention may also be achieved by transmembrane, transdermal or other topical administrative routes using appropriate continuous release devices such as a supporting matrix, where applicable. The compositions of the invention may be formulated with conventional excipients, such as a filler, a disintegrating agent, a binder, a lubricant, a flavoring agent and the like. These are formulated in a conventional manner.

The compounds may be administered neat or with a solid or liquid pharmaceutical carrier to a patient in need of such treatment. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from a disease involving smooth muscle cell proliferation must be subjectively determined by the attending physician. The variables involved include the specific disease state and the size, age and response pattern of the patient.

The ability of the compounds of the present invention to inhibit smooth muscle cell proliferation was established using isolated porcine nortic smooth muscle cells in a modification of the procedure of Casteliot et al. J. Biol. Chem 257(19) 11256 (1982), as follows:

Fresh porcine aortas, scrupulously cleansed of fatty tissue, are rinsed in sterile phosphate-buffered saline with 2% antibiotic-antimycotic (100×) liquid ( 10,000 units of penicillin (base), 10,000 µg of streptomycin (base), and 25 µg of amphotericin B/mL utilizing penicillin G (sodium salt), streptomycin sulfate, and amphotericin B as Fungizone® in 0.85% saline, available from Gibco Laboratories, Grand Island Biological Co., Grand Island, N.Y.). The tissue is then digested in 10–15 mL of an enzyme solution containing collagerinse type I, 165 U/mL; elastase type III, 15 U/mL; BSA, 2 mg/mL; and soybean trypsin inhibitor, 0.375 mg/mL, followed by incubation at 37° C. under 5% $CO_2$ atmosphere for 10 to 15 minutes. After this treatment, the outer surface adventitia is removed by peeling with a forceps. The aorta is then longitudinally cut and laid open and the endothelial layer is removed by scraping.

The medial layer of cells is rinsed in the enzyme solution, and placed in a new 100 mm dish with 10 mL of enzyme solution. The medial layer of cells is minced using a fine pair of scissors and digested for 2–3 hours at 37° C. in 30 mL of fresh enzyme solution. After digestion, the medial tissue is homogenized using a sterile Pasteur pipette with a fire polished tip or an Eppendorf pipetter with a 200–1000 gL sterile pipette tip. The suspension is then centrifuged for 10 minutes at 8000 rpm and the pellet is suspended in 4–6 mL of fresh enzyme solution and plated onto 4–6 100 mm flasks with vented caps. The cells are then allowed to grow to confluence and split using 0.25% trypsin. The cells are evaluated for purity and overall quality using antibody to SMC actin.

The cells are assayed in early passage (generally passage 3–7) at sub-confluent conditions. Cultures are grown in 16 mm (24 well) multi-well culture dishes in media 199 supplemented with 10% fetal bovine serum and 2% antibiotic/antimycotic. At subconfluence, the cells are placed in a defined serum free, lymphocyte medium (AIM-V; Gibeo) for 24–48 hours prior to initiating the experimental protocol.

The standard test procedure is initiated by addition of the test compound, $^3$H-thymidine and serum or a specific growth factor to the serum deprived synchronized cells. Growth factor and serum stimulations are optimized for each cell type. The test compounds are added to each well at 50 fold dilution (20 µL/well) and the plates are incubated for 24–36 hours at 37° C. in 5% $CO_2$ atmosphere. Test compounds are dissolved in 50% ethanol and assayed at 1, 10, and 100 µM. As a control, RG 50872 (Bilder, G. A.; et al., Am. J. Cell Physiol., 1991; 260: C721) is routinely assayed under the conditions of each cell preparation at a concentration of 5 µM.

At the completion of the experiment, the plates are placed on ice, washed three times with ice cold PBS and incubated in ice cold 10% trichloroacetic acid (TCA) for 30 minutes to remove acid soluble proteins. Each solution is transferred to a scintillation vial containing 0.4N HCl (500 µL/vial to neutralize NaOH) and each well is rinsed two times with water (500 µL) for a total volume of 2 mL/vial.

Data is quantitated by subjecting the vials to a scintillation counter, in triplicate, for both control and experimental samples. Control (100%) data is obtained from maximally stimulated cells, as the result of growth factor or serum stimulation. Experimental data is obtained from cells maximally stimulated with growth factor or serum and treated with a test compound. (The platelet-derived growth factor used in the assay was human recombinant PDGF-AB purchased from Upstate Biotechnology Inc., Lake Placid, N.Y.). Data is expressed as a percent of control from which $IC_{50}$s are determined.

To distinguish cytotoxicity from the ability of a compound to prevent proliferation, the test compounds were examined using a commercial modification of the MTT assay. Briefly, cells were grown in 24 well plates to 70–80% confluency. The cells were serum deprived for 24–48 hours prior to initiation of the experimental protocol. To insure that the MTT assay monitored toxicity rather than proliferation, the cells were incubated with 50 mM test compound in fresh medium without serum for 24 hours at 37° C. in a humidified $CO_2$ incubator. Upon completion of the compound treatment, MTT indicator dye was added for 4 hours at 37° C. Cells were then solubilized and aliquots from each well were transferred to a 96-well plate for analysis. Absorbance at 570 nm wavelength with a reference wavelength of 630 um was recorded using an ELISA plate reader. Results are reported as percent viable using no drug (100% viable) and pre-solubilization (0% viable) standards.

The compounds of the present invention are effective inhibitors of smooth muscle cell proliferation as shown by the data presented in Table I.

TABLE I

| Compound of Example Number | Porcine Smooth Muscle Cell Antiproliferation $IC_{50}$ or % Inhibition at x Concentration | | Cytotoxicity % Viable Cells |
|---|---|---|---|
| | Serum | PDGF | |
| 1 | 39.8%/10 µM | 4.4 µM | 90 |
| 2 | 38.4%/10 µM | 1.1 µM | 65 |
| 3 | 41.3%/10 µM | 2.47 µM | 82 |
| 4 | 0.66 µM | 0.76 µM | 84 |

The following examples are presented by way of illustration rather than limitation for the production of representative compounds of the invention.

EXAMPLE 1

1-(3,4-Dichlorobenzyl)-2-pyridin-2-yl-1H-benzoimidazole

2-Pyridin-2-yl-1H-benzoimidazole (1.95 g, 0.01 mol) was dissolved in DMF (50 mL) under an atmosphere of nitrogen. Sodium hydride (60% dispersion in oil, 0.48 g, 0.012 mol) was then added. The reaction mixture was stirred at ambient temperature for 0.5 hour. 3,4-Dichlorobenzyl bromide (2.4 g, 0.01 mol) was then added. The mixture was stirred at 80° C. for a period of 4 hours. The mixture was cooled and diluted with water. The mixture was then extracted with ethyl acetate. The organic extract was washed with water twice then evaporated. The residue was triturated with a small amount of ethyl acetate/hexane. The solid was collected and crystallized from ethanolic hydrogen chloride. The solid was collected to give the title compound (1.3 g, 36.7% yield) as a mono-hydrochloride, light brown solid, m.p. 227°–229° C. Anal. Calcd. for $C_{19}H_{13}Cl_2N_3$·HCl: C, 58.41; H, 3.61; N, 10.76. Found: C, 58.21; H, 3.54; N, 10.80. Mass spectrum (+FAB; [M+H]$^+$) 354/356/358. $^1$H-NMR (DMSO-$d_6$; 400 MHz) δ 8.78 (d, 1H), 8.52 (d, 1H), 8.15 (t, 1H), 7.9 (d, 1H), 7.77 (d, 1H), 7.65 (d, 2H), 7.54 (d, 1H), 7.48–7.52 (m, 2H), 7.23 (d, 1H), and 6.22 ppm (s, 2H).

EXAMPLE 2

4-[2-(Pyridin-2-yl)-benzoimidazol-1-ylmethyl]-benzoic acid methyl ester

The title compound was prepared using the procedure described in Example using (2.29 g, 0.01 mol) of 4-bromomethyl benzoic acid methyl ester. Crystallization from ethyl acetate/hexane mixture afforded 1.3 g (37.9% yield) of the title compound as a brown solid, m.p. 158°–159° C. Anal. Calcd. for $C_{21}H_{17}N_3O_2$: C, 73.45; H, 4.99; N, 12.24. Found: C, 73.47; H, 5.07; N, 12.21. Mass spectrum (+FAB; [M+H]$^+$) 344. $^1$H-NMR (DMSO-$d_6$; 400 MHz) δ 8.63 (d, 1H), 8.38 (d, 1H), 7.98 (t, 1H), 7.84 (d, 2H), 7.77 (m, 1H), 7.54 (m, 1H), 7.47 (m, 1H), 7.28 (m, 2H), 7.24 (d, 2H), 6.28 (s, 2H), and 3.78 ppm (s, 3H).

EXAMPLE 3

4-(5,6-Dimethyl-2-trifluoromethyl-benzoimidazol-1-ylmethyl)-benzoic acid methyl ester 5,6-Dimethyl-2-trifluoromethyl-1H-benzoimidazole (2.14 g, 0.01 mol) was dissolved in DMF (50 mL). Sodium hydride (60% dispersion in oil, 0.48 g, 0.012 mol) was added and the reaction mixture was stirred at ambient temperature for 0.5 hour under an atmosphere of nitrogen. 4-Bromomethyl benzoic acid methyl ester (2.29 g, 0.01 mol) was then added. The mixture was stirred at 80° C. for 18 hours. Most of the solvent was evaporated. The residue was diluted with water and extracted with ethyl acetate. The organic phase was washed with water, dried over anhydrous sodium sulfate then evaporated. The residue was crystallized from ethyl acetate/hexane twice to afford pure title compound (0.85 g, 23.5% yield) as a white solid, m.p. 150°–152° C. Anal. Calcd. for $C_{19}H_{17}F_3N_2O_2$: C, 62.98; H, 4.73; N, 7.73. Found: C, 62.96; H, 4.73; N, 7.56. Mass spectrum (+FAB; $[M+H]^+$) 363. $^1$H-NMR (DMSO-$d_6$; 400 MHz) δ 7.90 (d, 1H), 7.63 (s, 1H), 7.45 (s, 1H), 7.15 (d, 2H), 5.74 (s, 2H), 3.81 (s, 3H), 2.33 (s, 3H), and 2.30 ppm (s, 3H).

EXAMPLE 4

Step 1

Ethyl-butyroimidate hydrochloride

A solution of butyronitrile (15 g, 0.21 mol) in EtOH (150 mL) was cooled in an ice bath. The cold solution was then saturated with hydrogen chloride. The reaction mixture was refrigerated for 18 hours. The ethanol was evaporated under vacuum. The residual oily substance was then treated with ether to obtain the title compound (15.5 g, 48% yield) which was used in the next reaction.

Step 2

2-Propyl-5-nitrobenzimidazole

A mixture of ethyl-butyroimidate hydrochloride (7.6 g, 50 mmol) and 4-nitro-1,2-phenylenediamine (7.6 g, 50 mmol) in ethanol (100 mL) was refluxed for 18 hours. The ethanol was evaporated under vacuum. The sticky solid was suspended in $H_2O$ (100 mL). Separation of the yellow solid gave the title compound (5.3 g, 52% yield). $^1$H-NMR (DMSO-$d_6$; 200 MHz) δ 12.9 (s, 1H), 8.4 (s, 1H), 8.0–8.05 (d, 1H), 7.6–7.64 (d, 1H), 2.8–2.85 (t, 2H), 1.7–1.85 (m, 2H), 0.9–1.0 ppm (t, 3H).

Step 3

4-(5-Nitro-2-propyl-benzoimidazol-1-ylmethyl)-benzoic acid ethyl ester

To a suspension of sodium hydride, 60% dispersion in oil (1.0 g; 25 mmol) in DMF (30 ml), a solution of 2-propyl-5-nitrobenzimazole (4.2; 20 mol) in DMF (30 mL) was added dropwise over 10 minutes. After addition, the reaction mixture was stirred at ambient temperature for 30 minutes, then ethyl 4-(bromomethyl)benzoate (4.7 g; 20 mmol) was added. The reaction mixture was heated at 80° C. for 18 hours, then concentrated to a thick oil. The oil was extracted with ethyl acetate and water. The ethyl acetate layer was concentrated to dryness. The residue (1.3 g) was subjected to flash chromatography on silica gel (hexane/EtOAc; 7:3) to obtain 365 mg of yellow solid. Recrystallization from hexane/EtOAc gave the title compound, m.p. 136°–138° C. Anal. Calcd. for $C_{20}H_{21}N_3O_4$: C, 65.38; H, 5.74; N, 11.44. Found: C, 65.15; H, 5.75; N, 11.26. Mass spectrum (EI; $M^+$) m/z 367. $^1$H-NMR (DMSO-$d_6$; 400 MHz) δ 8.5 (d, 1H), 8.1 (dd, 1H), 7.9 (d, 2H), 7.7 (d, 1H), 7.2 (d, 2H), 5.7 (s, 2H), 4.3–4.3 (q, 2H), 2.8 (t, 2H), 1.7–2.0 (m, 2H), 1.24–1.3 (t, 3H), and 0.90–0.95 ppm (t, 3H).

What is claimed is:

1. A compound selected from the group consisting of 1-(3,4-dichlorobenzyl)-2-pyridin-2-yl-1H-benzoimidazole;

4-[2-(pyridin-2-yl)-benzoimidazol-1-ylmethyl]-benzoic acid methyl ester;

4-(5,6-dimethyl-2-trifluoromethyl-benzoimidazol-1-ylmethyl)benzoic acid methyl ester; and 4-(5-nitro-2-propyl-benzoimidazol-1-ylmethyl)-benzoic acid ethyl ester;

or a pharmaceutically acceptable salt thereof.

2. The compound of claim 1, which is 1-(3,4-dichlorobenzyl)-2-pyridin-2-yl-1H-benzoimidazole or a pharmaceutically acceptable salt thereof.

3. A compound selected from the group consisting of

4-[2-(pyridin-2-yl)-benzoimidazol-1-ylmethyl]-benzoic acid methyl ester;

4-(5,6-dimethyl-2-trifluoromethyl-benzoimidazol-1-ylmethyl)benzoic acid methyl ester; and 4-(5-nitro-2-propyl-benzoimidazol-1-ylmethyl)-benzoic acid ethyl ester;

or a pharmaceutically acceptable salt thereof.

4. The compound of claim 3 which is 4-[2-(pyridin-2-yl)-benzoimidazol-1-yl-methyl]-benzoic acid methyl ester or a pharmaceutically acceptable salt thereof.

5. The compound of claim 3 which is 4-(5,6-dimethyl-2-trifluoromethyl-benzoimidazol-1-ylmethyl)benzoic acid methyl ester or a pharmaceutically acceptable salt thereof.

6. The compound of claim 3 which is 4-(5-nitro-2-propyl-benzoimidazol-1-yl-methyl)-benzoic acid ethyl ester or a pharmaceutically acceptable salt thereof.

* * * * *